United States Patent
McClure et al.

[11] Patent Number: 6,145,991
[45] Date of Patent: Nov. 14, 2000

[54] RULE BASED VISUAL FIELD AUTOINTERPRETATION SYSTEM

[75] Inventors: Richard J. McClure; Dariusz Wroblewski, both of San Diego; R. Kemp Massengill, Leucadia, all of Calif.

[73] Assignees: Virtual-Eye.com, Inc., Leucadia; Orincon Corp., San Diego, both of Calif.

[21] Appl. No.: 09/430,863

[22] Filed: Nov. 1, 1999

Related U.S. Application Data

[60] Provisional application No. 60/106,648, Nov. 2, 1998.

[51] Int. Cl.⁷ ........................................................ A61B 3/00
[52] U.S. Cl. ............................................................. 351/246
[58] Field of Search ...................................... 351/222, 224, 351/226, 246, 206; 706/924; 128/904, 903; 600/301

[56] References Cited

U.S. PATENT DOCUMENTS

| | | | |
|---|---|---|---|
| 5,623,925 | 4/1997 | Swenson et al. | 128/630 |
| 5,894,338 | 4/1999 | Miehle et al. | 351/206 |
| 6,033,076 | 3/2000 | Braeuning et al. | 351/224 |

*Primary Examiner*—George Manuel
*Attorney, Agent, or Firm*—Gerald W. Spinks

[57] ABSTRACT

A system and method for automatically interpreting the results of visual field tests with a computer programmed to perform a continuously updated protocol derived from the interpretation of numerous visual field tests by experts in interpretation of visual field test results.

17 Claims, No Drawings

RULE BASED VISUAL FIELD AUTOINTERPRETATION SYSTEM

CROSS REFERENCE TO RELATED APPLICATIONS

This application relies for priority upon U.S. Provisional Patent Application Serial No. 60/106,648, filed Nov. 2, 1998.

BACKGROUND OF THE INVENTION

1. Field of the Invention

This invention is in the field of gathering and interpreting data on the visual field of a patient, and making clinical diagnoses.

2. Background Information

Visual field interpretation, as it is commonly practiced today, is severely hampered by the fact that two practitioners will frequently come to different conclusions when interpreting a given visual field. One will call the visual field "normal," while another will classify the visual field as "abnormal."

The problem is that most eye-care practitioners throughout the world are generalists by training, rather than glaucoma specialists, neurologists, or neuro-ophthalmologists. Not having had the additional years of rigorous training associated with glaucoma, neurology or neuro-ophthalmology subspecialization, the average generalist therefore lacks the expertise to consistently interpret subtle visual fields with requisite accuracy. Grossly abnormal visual fields are readily diagnosed, but subtly abnormal, or equivocal, visual fields are often misdiagnosed, or called "normal." This diagnostic crudeness is an obvious disservice to patients.

For example, many patients with insidious forms of glaucoma, such as low-tension glaucoma, are not treated because of a generalist eye-care practicioner's inability to diagnose subtle, but yet abnormal, visual field deficits. Because patients with low-tension glaucoma have a normal, or even low, intraocular pressure, the patient is told with assurance that no disease is present, and that he or she is "fine." Nothing could be further from the truth: This patient is subject to the ravages of untreated glaucoma, which causes permanent and irreversible visual loss and much disability.

Although other tests for glaucoma have positive value, the instruments required to perform these tests, such as a laser scanner, are prohibitively expensive for most practitioners and small offices. Visual field testing, therefore, remains the "gold standard" for diagnosing diseases of the optic nerve and the visual system.

How can the accuracy of visual field testing be improved? Of interest is the autointerpretation of visual fields, especially with automated data classification systems, such as neural networks, for processing visual fields.

Neural nets have great advantages, in that they are unbiased and, as the neural net is "intelligent" and "learns" as the data base enlarges, neural nets have great flexibility.

DETAILED DESCRIPTION OF THE INVENTION

For comparison with the results yielded by neural network based systems, and for further validation of other visual field autointerpretation work, the use of a rule-based expert system has merit.

In a rule-based expert data classification system, the independent interpretations of experts for a large number of visual fields are reduced to code, and then to explicit "rules," and these codified rules are then used to interpret subsequent visual fields.

For instance, if ten of the best glaucoma specialists in the world, ten of the best neurologists, ten of the best neuro-ophthalmologists, and ten of the best optometrists, are asked to interpret a large number of visual fields obtained from patients, and then to classify these visual fields into normal, abnormal, or equivocal categories, and to specify the disease category corresponding to each abnormal visual field, the result is that a data base is developed which can then be codified. This codification is analyzed carefully, and explicit rules are then created which can be applied to visual field testing in general.

An advantage of a rule-based expert system is that practitioners throughout the world would likely feel quite comfortable applying the rules of these glaucoma specialists, neurologists, neuro-ophthalmologists, and optometrists to their own visual field practices. It would be as if a world-famous group of visual field experts is brought into the office for consultation for a visual field test. Therefore, every practitioner would greatly benefit from the combined expertise of the group of world-class experts.

To avoid having a rule-based expert system that is ossified and, figuratively speaking, cast in stone, the experts are continually consulted, their updated opinions and interpretations are continually recodified, and the new rules are merged with the previous rules.

A rule-based expert system according to the present invention would utilize the following personnel, all of whom, it should be emphasized, are experts in visual field performance and interpretation:

1. 10 glaucoma sub-specialists;
2. 10 neurologists;
3. 10 neuro-ophthalmologists; and,
4. 10 optometrists.

The steps of building the rule-based autointerpreter are as follows:

1. Initially, approximately five hundred sets of visual field data, or more, are presented to each of these experts, along with a detailed clinical history and pertinent physical findings.
2. The opinions of all of these experts are subsequently analyzed and codified.
3. A set of explicit rules is then developed, based upon the information codified from the expert interpretations.
4. These explicit rules are incorporated into an automated diagnostic system, such that when the automated system is presented with a subsequent visual field and appropriate data, such as, for instance, visual acuity, and, if known, clinical history or other pertinent physical findings, the rule-based expert system autointerprets the visual field and suggests a clinical diagnosis.
5. The first decision by the rule-based expert autointerpretation system is to determine whether the visual field is:
   A. Normal;
   B. Abnormal; or,
   C. Equivocal.

If "normal," no further classification is required. If "abnormal," the rule-based expert autointerpreter states the suspected diagnosis, or diagnoses. Recommendations are made regarding further tests (such as CAT-scan, MRI, serial intraocular pressures at different times of the day, intraocular pressure upon dilation of the pupil, and other examinations). If "equivocal," as is sometimes the case for a variety of reasons, including poor concentration on the part of the patient, this fact is stated to the practicioner. The choices are to repeat the visual field on another day, or to perform ancillary tests, such as the laser scan, if available.

Oftentimes, with equivocal visual fields, the visual field test is recommended to be repeated in three or four months. If a disease state is present, by this later time, an equivocal visual field may well be no longer "equivocal," but definitely "abnormal." The most important consideration is that equivocal visual fields must be recognized as such, for calling such a test "normal" generally means that a particular patient may not receive visual field testing for a long time, and sometimes, never again. Critical pathology will then most assuredly be missed.

The means of implementation of the rule-based expert system will now be described. This rule-based expert auto-interpretation system can be locally attached to the practitioner's visual field machine (either a conventional globe, a frequency doubling testing instrument, a head-mounted display [HMD] system, or any other kind of visual field analyzer) and can be utilized locally within the practitioner's office, or, preferably, a rule-based expert system can be used in telemedicine.

The great advantage of telemedicine is that the rule-based system can be continually upgraded, by a team of scientists, who will consult with the panel of experts on a timely basis, for instance, every 6 to 12 months, and take new information from these expert consultations to revise and upgrade the rule-based expert autointerpretation system, creating an updated explicit set of rules.

The vehicle of choice for telemedicine is the Internet, which is growing by leaps and bounds and now has worldwide capability. Visual field interpretation can be performed globally utilizing a central monitoring station to service the entire world, or, if culturally required, monitoring stations can be deployed in various countries (i.e., France, Germany, Japan, Argentina, etc.) or geographical areas (i.e., Europe, Asia, Latin America, etc.).

The visual field test is interactively performed, with feedback to and from the patient. Utilizing telemedicine, diagnoses can be suggested virtually instantaneously, and treatment protocols can be instituted without delay. This method for performing visual fields featuring autointerpretation and telemedicine will enhance glaucoma diagnosis throughout the world.

It is the telemedicine component which allows for great facility in updating and upgrading the rule-based expert system. As we update the rules in concert with a chosen panel of experts, we will render uniform throughout the world the latest rules for visual field interpretation postulated by these acknowledged experts. Restricting the system to a purely local rule-based autointerpretation system for visual fields would create the likelihood that the system would not be updated and upgraded, but rather would become mired in unavoidable obsolescence. The novel telemedicine component makes a rule-based expert system globally upgradable simply by updating the software at the central, or regional, telemedicine stations.

In summary, the use of this rule-based expert system allows visual field performance monitoring and autointerpretation with greatly increased accuracy, compared to the present. By incorporating the telemedicine component of this invention, visual field performance and autointerpretation can readily become a reality on a world-wide basis.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A method for diagnosing a visual disorder in a patient, comprising:

performance of visual field tests on a statistically significant number of data-base patients;

interpretation of said visual field tests by at least three practitioners licensed to perform visual field test interpretation;

codification of results of said interpretations of said visual field test results into a set of interpretive rules to establish a protocol for interpreting visual field test results;

programming a computer to perform said protocol; performance of a visual field test on a visual field analyzer for diagnosis of a patient; and interpretation of results of said diagnostic visual field test by said computer performing said protocol.

2. A method as recited in claim 1, wherein said diagnostic visual field test is performed on said patient at a location remote from the location of said computer, further comprising:

transmitting results of said diagnostic visual field test from said remote location to said computer via the Internet; and transmitting said interpretation of said results of said diagnostic visual field test to said remote location via the Internet.

3. A method as recited in claim 1, further comprising:

obtaining clinical histories of said data-base patients; and interpretation of said visual field tests in view of said clinical histories by said at least three practitioners.

4. A method as recited in claim 1, compiling physical findings on said data-base patients; and interpretation of said visual field tests in view of said physical findings by said at least three practitioners.

5. A method as recited in claim 1, wherein said interpretation of said diagnostic visual field test by said computer performing said protocol comprises classification of said diagnostic visual field as one of the conditions selected from the group consisting of Normal, Abnormal, and Equivocal.

6. A method as recited in claim 1, further comprising:

obtaining a clinical history of said patient;

compiling physical findings on said patient; and interpretation of said results of said diagnostic visual field test by said computer performing said protocol, in view of said clinical history and said physical findings.

7. A method as recited in claim 1, further comprising periodic revision of said protocol through interpretation of additional visual field tests.

8. A method as recited in claim 1, wherein at least one of said practitioners is an opthalmologist.

9. A method as recited in claim 1, wherein at least one of said practitioners is an optometrist.

10. A method as recited in claim 1, wherein at least one of said practitioners is a neuro-opthalmologist.

11. A method as recited in claim 1, wherein at least one of said practitioners is a neurologist.

12. A method as recited in claim 1, wherein at least one of said practitioners is a glaucoma specialist.

13. A method as recited in claim 1, further comprising performance of visual field tests on at least 500 data-base patients.

14. A method as recited in claim 1, further comprising interpretation of said visual field tests by at least 10 practitioners in each of a plurality of disciplines.

15. A method as recited in claim 14, wherein said disciplines are selected from the group including opthalmologists, optometrists, neuro-opthalmologists, neurologists, and glaucoma specialists.

16. A method for diagnosing a visual disorder in a patient, comprising:

performance of visual field tests on a statistically significant number of data-base patients;

obtaining clinical histories of said data-base patients;

compiling physical findings on said data-base patients;

interpretation of said visual field tests, clinical histories, and physical findings by at least three practitioners licensed to perform visual field test interpretation;

codification of results of said interpretations of said visual field test results to establish a protocol for interpreting visual field test results;

programming a computer to perform said protocol;

performance of a visual field test for diagnosis of a patient on a visual field analyzer at a location remote from the location of said computer;

transmitting results of said diagnostic visual field test from said remote location to said computer via the Internet;

interpretation of results of said diagnostic visual field test by said computer performing said protocol; and transmitting said interpretation of said results of said diagnostic visual field test to said remote location via the Internet.

17. A system for diagnosing a visual disorder in a patient, comprising:

a computer programmed to perform a protocol for interpreting visual field test results, said protocol being derived from codification by at least three praciticners licenced to perform visual field test interpretation of a plurality of visual field test interpretations into a set of interpretive rules;

a visual field analyzer at a location remote from the location of said computer;

means for transmitting results of a diagnostic visual field test from said remote visual field analyzer to said computer via the Internet; and means for transmitting an interpretation of said results of said diagnostic visual field test to said remote location via the Internet.

* * * * *